United States Patent
Edahiro et al.

(10) Patent No.: US 9,163,014 B2
(45) Date of Patent: Oct. 20, 2015

(54) CRYSTALS OF PYRROLOQUINOLINEQUINONE SODIUM SALTS

(75) Inventors: Junichi Edahiro, Niigata (JP); Hitoshi Sakamoto, Niigata (JP); Kazuto Ikemoto, Niigata (JP); Hajime Shimizu, Niigata (JP); Tatsuya Hasegawa, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 341 days.

(21) Appl. No.: 13/383,472

(22) PCT Filed: Jun. 9, 2010

(86) PCT No.: PCT/JP2010/059761
§ 371 (c)(1),
(2), (4) Date: Jan. 11, 2012

(87) PCT Pub. No.: WO2011/007633
PCT Pub. Date: Jan. 20, 2011

(65) Prior Publication Data
US 2012/0116087 A1 May 10, 2012

(30) Foreign Application Priority Data

Jul. 16, 2009 (JP) ................. 2009-168087

(51) Int. Cl.
*C07D 471/04* (2006.01)
*A23L 1/30* (2006.01)

(52) U.S. Cl.
CPC ............ *C07D 471/04* (2013.01); *A23L 1/30* (2013.01); *C07B 2200/13* (2013.01)

(58) Field of Classification Search
CPC .............. C07D 471/04; C07B 2200/03
USPC ........................................ 546/84
See application file for complete search history.

(56) References Cited

U.S. PATENT DOCUMENTS 5,061,711 A * 10/1991 Urakami et al. ............... 514/292
2011/0313164 A1* 12/2011 Zhong et al. .................... 546/84

FOREIGN PATENT DOCUMENTS

| CN | 101885725 A | 11/2010 |
| EP | 2 062 892 A1 | 5/2009 |
| JP | 62 246575 | 10/1987 |
| JP | 64 75487 | 3/1989 |
| JP | 1 218597 | 8/1989 |
| JP | 2 67284 | 3/1990 |

OTHER PUBLICATIONS

Decomposition of commercial vegetable oils, Dweck et al., 2004.*
Office Action issued Dec. 30, 2013, in Chinese Patent Application No. 201080031945.X (with English-language Translation).
Extended European Search Report issued Sep. 26, 2012 in Patent Application No. 10799695.1.
U.S. Appl. No. 14/125,788, filed Jan. 9, 2014, Ikemoto et al.
Ishida, T., et al., "Molecular and Crystal Structures of PQQ (Methoxatin), a Novel Coenzyme of Quinoproteins: Extensive Stacking Character and Metal Ion Interaction," Journal of American Chemical Society, vol. 111, pp. 6822-6828, (1989).
"A new redox-cofactor vitamin for mammals," Nature, vol. 422, p. 832, (Apr. 24, 2003).
Corey, E.J. et al., "Total Synthesis of the Quinonoid Alcohol Dehydrogenase Coenzyme (1) of Methylotrophic Bacteria," Journal of American Chemical Society, vol. 103, pp. 5599-5600, (1981).
International Search Report Issued Aug. 17, 2010 in PCT/JP10/59761 Filed Jun. 9, 2010.
International Preliminary Report on Patentability Issued Feb. 7, 2012 in PCT/JP10/59761 Filed Jun. 9, 2010.

* cited by examiner

*Primary Examiner* — Rita Desai
(74) *Attorney, Agent, or Firm* — Oblon, McClelland, Maier & Neustadt, L.L.P.

(57) ABSTRACT

A crystal of pyrroloquinoline quinone disodium salt having peaks at 2θ of 9.1°, 10.3°, 13.8°, 17.7°, 18.3°, 24.0°, 27.4°, 31.2° and 39.5° (±0.2° for each) in powder X-ray diffractometry using Cu Kα radiation, or a crystal of pyrroloquinoline quinone trisodium salt having peaks at 2θ of 6.6°, 11.4°, 13.0°, 22.6°, 26.9°, 27.9°, 37.0°, 38.9° and 43.4° (±0.2° for each) in powder X-ray diffractometry using Cu Kα radiation.

18 Claims, 6 Drawing Sheets

CRYSTALS OF PYRROLOQUINOLINEQUINONE SODIUM SALTS

TECHNICAL FIELD

The present invention relates to a novel crystal of a sodium salt of pyrroloquinoline quinone and a method for producing it.

BACKGROUND ART

Since it has been proposed that pyrroloquinoline quinone (PQQ) may be a novel vitamin, it has drawn attention (see, for example, Non-patent Document 1). PQQ exists in not only bacteria but also in molds and yeasts, which are eukaryotes, and plays important roles as a coenzyme. Further, PQQ has so far been known to have a number of bioactivities such as the cell growth-promoting action, anti-cataract action, liver disease-preventing/curing action, wound-healing action, anti-allergic action, reverse transcriptase-inhibiting action, glyoxalase I-inhibiting action, carcinostatic action and nerve fiber-regenerating action.

PQQ can be produced by an organic chemical synthetic method (Non-patent Document 2), fermentation method (Patent Document 1) or the like. However, since PQQ obtained by these methods contains large amounts of water and impurities, a technology to obtain crystals of PQQ which are stable and highly pure has been demanded.

Crystals of a sodium salt of PQQ which were shown to be single crystal by X-ray crystallography have been obtained by evaporative concentration of the disodium salt of PQQ in phosphate buffer (Non-patent Document 3). However, this method is not suitable for mass production. Further, in a method by salting-out, since a salt used in a large amount, such as NaCl, is contaminated in the precipitated solids, there are drawbacks in that an operation of removal of the existing salt is required and that analysis for securing stable quality is difficult because of the salt.

As a method for obtaining crystals of PQQ having no such drawbacks, a method wherein a water-soluble organic solvent is added to cause recrystallization has been reported (Patent Document 2). However, there is no information on the crystal form in this literature, and, when the present inventors carried out a confirmatory experiment for recrystallization using ethanol, it was confirmed that the crystallinity of the disodium salt of PQQ was low and ethanol used as a solvent was likely to remain even after drying, so that it was difficult to provide crystals having stable quality. Further, the ethanol recrystallization method has a drawback in that the method requires a cooling apparatus for precipitating solids, which increases the cost of the process.

Further, in terms of the trisodium salt of PQQ, there has been no report on its crystal so far, unlike the disodium salt.

PRIOR ART DOCUMENTS

Patent Documents

Patent Document 1: JP 2751183 B
Patent Document 2: JP 7-113024 A

Non-Patent Documents

Non-patent Document 1: Nature, vol. 422, 24 April, 2003, p. 832
Non-patent Document 2: JACS, vol. 103, pp. 5599-5600 (1981)
Non-patent Document 3: JACS, vol. 111, pp. 6822-6828 (1989)

SUMMARY OF THE INVENTION

In consideration of the pharmaceutical value of PQQ, it is important to reproducibly obtain stable high-purity crystals having a definite crystal form, which crystals can be stored for a long time without strictly controlling storage conditions such as the temperature, light, humidity and oxygen level. Therefore, the present invention aims to provide stable crystals of a sodium salt of PQQ and to provide a method for producing them.

The present inventors intensively studied to solve the above problems. As a result, the present inventors succeeded in obtaining novel high-purity crystals of sodium salts of PQQ, with which the above problems can be solved, by studying the conditions of crystallization of the sodium salts of PQQ, thereby completing the present invention.

The present invention is as follows.
(1) A crystal of pyrroloquinoline quinone disodium salt having peaks at 2θ of 9.1°, 10.3°, 13.8°, 17.7°, 18.3°, 24.0°, 27.4°, 31.2° and 39.5° (±0.2° for each) in powder X-ray diffractometry using Cu Kα radiation.
(2) A crystal of pyrroloquinoline quinone trisodium salt having peaks at 2θ of 6.6°, 11.4°, 13.0°, 22.6°, 26.9°, 27.9°, 37.0°, 38.9° and 43.4° (±0.2° for each) in powder X-ray diffractometry using Cu Kα radiation.
(3) A method for producing the crystal of pyrroloquinoline quinone disodium salt according to (1), said method comprising preparing an aqueous solution and/or suspension of pyrroloquinoline quinone trisodium salt comprising a 10 to 90 (v/v) % water-soluble organic solvent and adjusting pH of said aqueous solution and/or suspension to within the range of 2 to 5 to crystallize pyrroloquinoline quinone disodium salt.
(4) The method according to (3), wherein said water-soluble organic solvent is an alcohol.
(5) The method according to (4), wherein said alcohol is ethanol.
(6) The method according to any one of (3) to (5), wherein said crystallization is carried out in a suspended state.
(7) A method for producing the crystal of pyrroloquinoline quinone trisodium salt according to (2), said method comprising adding a water-soluble organic solvent to an aqueous solution and/or suspension of pyrroloquinoline quinone trisodium salt such that a concentration of 10 to 90 (v/v) % is attained while maintaining pH of the obtained aqueous solution and/or suspension within the range of 6 to 10, to crystallize pyrroloquinoline quinone trisodium salt.
(8) The method according to (7), wherein said water-soluble organic solvent is an alcohol.
(9) The method according to (8), wherein said alcohol is ethanol.
(10) A method for producing the crystal of pyrroloquinoline quinone trisodium salt according to (2), said method comprising performing salting-out while maintaining pH of an aqueous solution and/or suspension of pyrroloquinoline quinone trisodium salt within the range of 6 to 10, to crystallize pyrroloquinoline quinone trisodium salt.

(11) A functional food comprising the crystal of a sodium salt of pyrroloquinoline quinone according to (1) or (2).
(12) A pharmaceutical comprising the crystal of a sodium salt of pyrroloquinoline quinone according to (1) or (2).

By the present invention, highly pure and stable crystals of a sodium salt of PQQ can be provided, and a method of their stable production can be further provided.

DESCRIPTION OF THE EMBODIMENTS

In the present invention, pyrroloquinoline quinone (PQQ) means the substance having the structure represented by Formula 1:

Formula 1

The crystal of the first invention of the present application (hereinafter referred to as Crystal 1) is a crystal of PQQ disodium salt having peaks at the angle of reflection 2θ of 9.1°, 10.3°, 13.8°, 17.7°, 18.3°, 24.0°, 27.4°, 31.2° and 39.5° (±0.2° for each) in powder X-ray diffractometry using Cu Kα radiation.

Measurement of the angle of diffraction 2θ by powder X-ray diffractometry can be carried out under, for example, the following measurement conditions.
Apparatus: M18XCE, manufactured by MAC Science, Co. Ltd.
X-ray: Cu/40 kV tube voltage/100 mA tube current
Divergence slit: 1°
Scattering slit: 1°
Receiving slit: 0.3 mm
Scan speed: 4.000°/min.
Sampling width: 0.020°

The peaks can be monitored also with a common powder X-ray diffractometer equipped with a monochromator. Since the crystal form defined in the present invention contains measurement errors, the determination can be carried out as long as rational identities for the angles of the peaks are observed.

In the cases of PQQ disodium salt obtained by the conventional ethanol recrystallization method, such a large number of diffraction peaks did not appear, so that the conventionally obtained solids are considered to have low crystallinities.

Examples of the method for producing Crystal 1 include a method wherein PQQ trisodium salt is dissolved/suspended in water and a water-soluble organic solvent is added to the resulting solution and/or suspension such that a concentration of 10 to 90 (v/v) %, preferably 20 to 80 (v/v) % is attained, followed by adjusting pH to within the range of 2 to 5 to cause crystallization. Alternatively, the crystallization may be carried out by dissolving and/or suspending PQQ trisodium salt in a water-soluble organic solvent and adding water to the resulting solution and/or suspension such that the concentration of the water-soluble organic solvent becomes 10 to 90 (v/v) %, preferably 20 to 80 (v/v) %, followed by adjusting pH to within the range of 2 to 5. Alternatively, the crystallization may be carried out by dissolving and/or suspending PQQ trisodium salt in an aqueous medium containing a 10 to 90 (v/v) %, preferably 20 to 80 (v/v) % water-soluble organic solvent and adjusting pH to within the range of 2 to 5.

The PQQ trisodium salt to be used as a raw material can be produced by an organic chemical synthetic method (e.g., JACS, vol. 103, pp. 5599-5600 (1981)), fermentation method (e.g., JP 1-218597 A and JP 2692167 B) or the like. The PQQ trisodium salt to be used as a raw material may be either crystalline or amorphous. The PQQ trisodium salt may also contain impurities.

Particular examples of the water-soluble organic solvent which may be used include methanol, ethanol, n-propanol, isopropanol, ethylene glycol, propylene glycol, methoxyethanol, diethylene glycol, methoxydiethylene glycol, glycerin, methoxypropanol, acetone, methyl ethyl ketone, acetonitrile, ethyl lactate and methyl hydroxyisobutyrate. Among these, alcohols are more preferred, ethanol is especially preferred.

The organic solvent is used as a poor solvent for decreasing the solubility of PQQ, and the concentration of the organic solvent may be set appropriately within the above-described range depending on the initial amount of PQQ trisodium salt.

In a common method for producing crystals, solids are dissolved in a solvent and crystals are then precipitated by adding a poor solvent to the resulting solution.

However, in the present invention, the crystallization can be carried out even in a suspended state in which solids exist. Being able to carry out the operation even in a suspended state is preferred since the volume of the apparatus can be reduced and the amount of the waste liquid to be discharged can be reduced.

In a particular method of operation to obtain Crystal 1, an aqueous solution and/or suspension containing a raw material PQQ trisodium salt is first prepared. In this step, 0.5 to 80 g of PQQ trisodium salt per 1 L of water is preferably added. Subsequently, a water-soluble organic solvent is added to the aqueous solution and/or suspension to decrease the solubility of PQQ trisodium salt. Precipitation of solids in this step is not problematic. Thereafter, an acid may be added to the resulting solution/suspension while measuring pH, thereby adjusting the pH to within the range of 2 to 5.

Alternatively, PQQ trisodium salt may be added to, and dissolved and/or suspended in, a water-soluble organic solvent, followed by adding water to the resulting solution and/or suspension and then adjusting pH to within the range of 2 to 5, to cause crystallization. In this step, 0.5 to 800 g of PQQ trisodium salt is preferably added per 1 L of the total of the water-soluble organic solvent and the water added.

Alternatively, PQQ trisodium salt may be added to, and dissolved and/or suspended in, an aqueous medium containing a water-soluble organic solvent, followed by adjusting pH to within the range of 2 to 5, to cause crystallization. In this step, 0.5 to 800 g of PQQ trisodium salt is preferably added per 1 L of the aqueous medium.

The type of the acid to be added for the pH adjustment is not restricted, and examples thereof include inorganic acids such as hydrochloric acid, hydrobromic acid, hydroiodic acid, perchloric acid, nitric acid and sulfuric acid; and organic acids such as formic acid, acetic acid, propionic acid, butyric acid, trichloroacetic acid, methanesulfonic acid and benzenesulfonic acid; among which hydrochloric acid is preferred.

When the pH became stable at a prescribed value within the range of pH 2 to 5, precipitated crystals are separated by filtration, centrifugation or the like, and thereby Crystal 1 can be obtained.

When the water-soluble organic solvent is added to the aqueous solution and/or suspension containing PQQ trisodium salt, the temperatures of the both liquids are not restricted as long as the liquids are not frozen, and the temperatures are preferably −30° C. to 80° C. since a high temperature decreases the energy efficiency. When the water-soluble organic solvent is added and the acid is then added to adjust pH to within the range of 2 to 5, the temperature of the solution or suspension is not restricted as long as the liquid is not frozen, and the temperature is preferably 5° C. to 80° C. since a high temperature decreases the energy efficiency and a low temperature decreases the crystallization rate (speed). The liquid is preferably stirred as required and then left to stand. The stirring time may be, for example, 5 minutes to 7 days. The standing time may be, for example, 5 minutes to 15 days.

In the obtained solution, crystals of PQQ disodium salt (Crystal 1) are produced. In the later-mentioned Example 2, the purity calculated by high performance liquid chromatography was 99.5%, so that extremely highly pure PQQ crystals can be obtained by this crystallization method.

Crystal 1 may be a hydrated material, and whether or not Crystal 1 is hydrated is not restricted as long as it has the above-described peaks.

The crystal of the second invention of the present application (Crystal 2) is a crystal of PQQ trisodium salt having peaks at 2θ of 6.6°, 11.4°, 13.0°, 22.6°, 26.9°. 27.9°, 37.0°, 38.9° and 43.4° (±0.2° for each) in powder X-ray diffractometry using Cu Kα radiation. These peaks are defined by powder X-ray diffractometry using the same measurement method as in the case of the above Crystal 1.

Crystal 2 can be obtained by carrying out crystallization using an aqueous solution and/or suspension containing raw material PQQ trisodium salt as mentioned above at a pH within the range of 6 to 10.

The crystallization can be carried out by salting-out in the presence of sodium ions or precipitation by addition of a water-soluble organic solvent. Since, in the case of crystals of the trisodium salt, unlike the case of crystals of the disodium salt, existence of a large excess of sodium ions is unlikely to make the analysis difficult, salting-out can be employed without any problem. The crystals can be obtained by adjusting pH to within the range of 6 to 10 and performing salting-out by adding dietary salt, sodium sulfate, sodium nitrate, sodium phosphate or the like. The concentration of the salt is not restricted as long as the added salt can be dissolved, and the concentration is preferably not less than 0.2 wt % and not more than 30 wt %. In cases where pH of the aqueous solution and/or suspension is within the range of 6 to 10, the pH adjustment is not necessary.

In cases where a water-soluble organic solvent is added, examples thereof include methanol, ethanol, n-propanol, isopropanol, ethylene glycol, propylene glycol, methoxyethanol, diethylene glycol, methoxydiethylene glycol, glycerin, methoxypropanol, acetone, methyl ethyl ketone, acetonitrile, ethyl lactate and methyl hydroxyisobutyrate. Among these, alcohols are more preferred, ethanol is especially preferred. The water-soluble organic solvent is preferably added such that a concentration of 10 to 90 (v/v) %, more preferably 20 to 80 (v/v) % is attained.

Crystal 2 may also be a hydrated material, and whether or not Crystal 2 is hydrated is not restricted as long as it has the above-described peaks.

PQQ has many pharmacological effects such as the cell growth-promoting action, anti-cataract action, liver disease-preventing/curing action, wound-healing action, anti-allergic action, reverse transcriptase-inhibiting action, glyoxalase I-inhibiting action, carcinostatic action and nerve fiber-regenerating action.

Therefore, Crystal 1 and Crystal 2 of PQQ of the present invention can be used as effective ingredients of pharmaceuticals and functional foods. That is, the crystals can be provided in the forms of external preparations for the skin, injection solutions, oral preparations and suppositories; and in the forms of foods and beverages taken regularly, dietary supplements, various hospital diets and the like. Examples of additives used for their preparation include liquids such as water; sugars such as fructose and glucose; oils such as peanut oil, soybean oil and olive oil; and glycols such as polyethylene glycol and polypropylene glycol. For solid preparations such as tablets, capsules and granules, examples of vehicles include, but are not limited to, sugars such as lactose, sucrose and mannitol; examples of lubricants include, but are not limited to, kaolin, talc and magnesium stearate; examples of disintegrators include, but are not limited to, starch and sodium alginate; examples of binders include, but are not limited to, polyvinyl alcohol, cellulose and gelatin; examples of surfactants include, but are not limited to, fatty acid esters; and plasticizers include, but are not limited to, glycerin. Solubilizers, fillers and the like may also be added as required.

Further, PQQ may be used either alone or in combination with other materials. Examples of materials which may be used in combination include, but are not limited to, vitamins such as vitamin B complex, vitamin C and vitamin E; amino acids; astaxanthin; carotenoids such as α-carotene and β-carotene; ω3 fatty acids such as docosahexaenoic acid and eicosapentaenoic acid; and ω6 fatty acids such as arachidonic acid.

Since the PQQ crystals of the present invention (Crystal 1 and Crystal 2) are highly pure and excellent in stability under preservation, these can be stored for a long time and preferably used as effective ingredients of pharmaceuticals and functional foods.

The present invention will now be described in more detail by way of Examples below, but the present invention is not restricted thereto.

EXAMPLES

Reference Example 1

Raw material PQQ trisodium salt was obtained as follows.
According to Example 1 of JP 2692167 B, *Hyphomicrobium denitrificance* DSM1869 was cultured, and the obtained culture was centrifuged to remove bacterial cells, to obtain the culture supernatant containing PQQ. This strain can be obtained from DSM (Deutsche Sammlung von Mikroorganismen (German Collection of Microorganisms and Cell Cultures).

The culture supernatant was passed through a Sephadex G-10 column (manufactured by Pharmacia) to allow adsorption of PQQ, and elution was performed with an aqueous NaCl solution to obtain an aqueous PQQ solution at pH 7.5, followed by further adding NaCl to the solution to a concentration of 60 g/L and cooling the resulting solution, thereby obtaining PQQ trisodium salt. The PQQ purity of the obtained PQQ trisodium salt was 99.0% as determined by UV absorption measured using high performance liquid chromatography.

The sodium salt of PQQ was analyzed under the following conditions. The PQQ concentration and purity were measured by high performance liquid chromatography under the conditions described below. Thereafter, the concentration of Na contained in the same solution was measured by cation chromatography under the conditions described below. Further, based on the concentrations of PQQ and Na contained in the above solution, the ratio of the amounts of the substances PQQ and Na contained in the sodium salt of PQQ was determined. In cases where this ratio of the amounts of the substances is 2.0±0.2, the salt is PQQ disodium salt, while in cases where the ratio is 3.0±0.2, the salt is PQQ trisodium salt.

(PQQ Analysis)
  Apparatus: high performance liquid chromatography LC-20A, manufactured by Shimadzu Corporation)
  Column: YMC-Pack ODS-TMS (5 μm), 150×4.6 mm I.D.
  Measuring temperature: 40° C.
  Detection: Absorbance at 260 nm
  Eluent: 100 mM $CH_3COOH$/100 mM $CH_3COONH_4$ (30/70, pH 5.1)
  Elution rate: 1.5 mL/min.

(Na Analysis)
  Pump: LC-6A, manufactured by Shimadzu Corporation
  Column oven: HIC-6A, manufactured by Shimadzu Corporation
  Measuring temperature: 40° C.
  Detector: Conductivity meter CM-8000, manufactured by Tosoh Corporation
  Column: Shodex, IC Y-521, manufactured by Showa Denko K. K.
  Eluent: 4 mM $HNO_3$
  Elution rate: 1.0 mL/min.

Example 1

(Crystallization) Crystals of PQQ Disodium Salt

Figure 1:
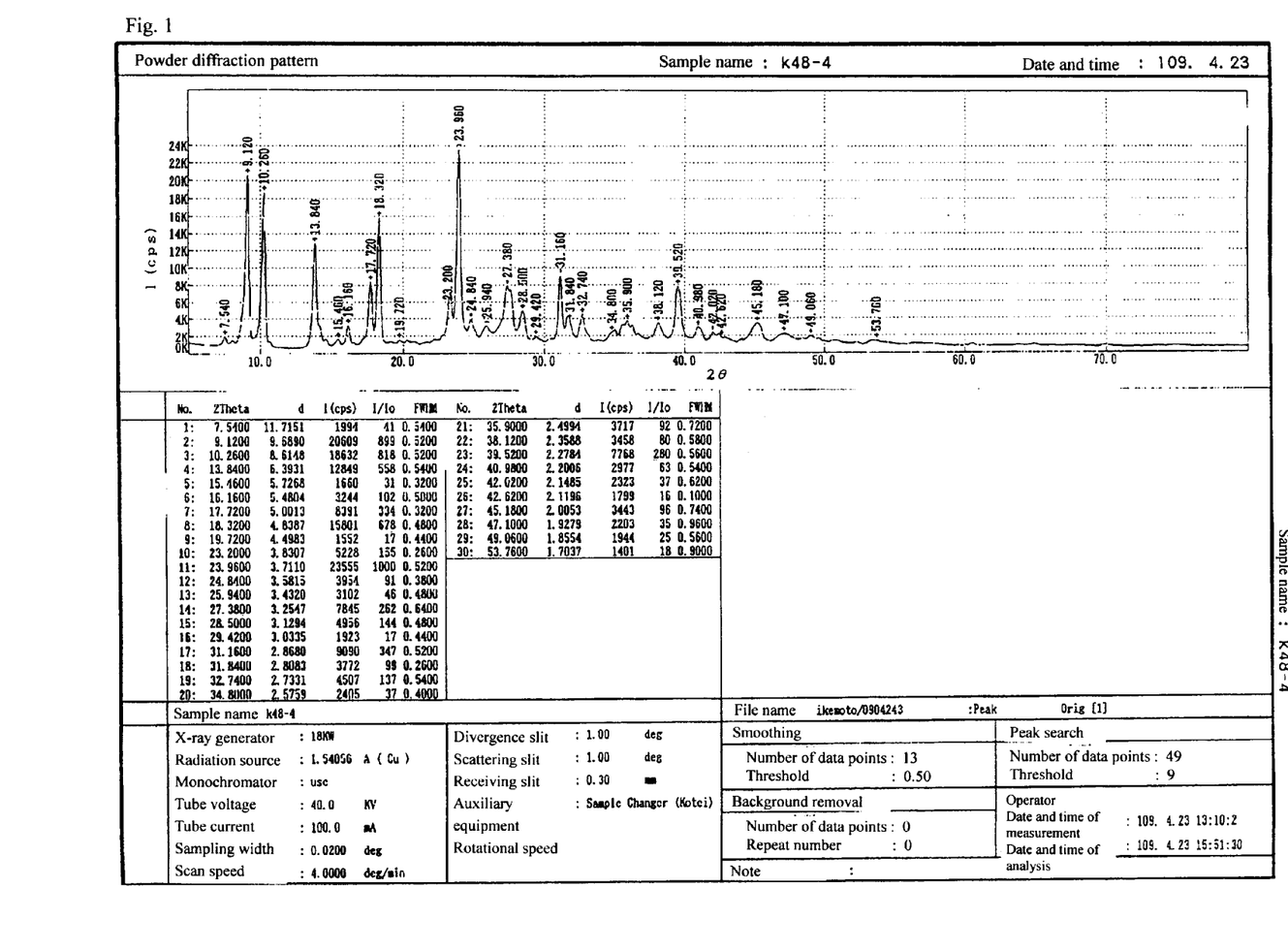
FIG. 1 is a diagram showing a powder X-ray diffraction spectrum of the crystals obtained in Example 1.

The PQQ trisodium salt prepared in Reference Example 1 was completely dissolved in ion-exchanged water, to prepare 500 g of a solution containing 12 g/L PQQ. To this solution, 500 mL of ethanol was added. At this time, red solids were precipitated. While measuring pH using a pH meter, hydrochloric acid was added dropwise to the resulting mixture to adjust pH to 3.6, followed by stirring the mixture at room temperature for 1 hour. Crystals were recovered by suction filtration and dried under reduced pressure at room temperature for 16 hours. As a result, crystals of PQQ disodium salt were obtained in a yield of 95 mol %. The powder X-ray diffraction spectrum of the obtained crystals was measured under the conditions described below. The results are shown in FIG. 1. Peaks at 2θ of 9.1°, 10.3°, 13.8°, 17.7°, 18.3°, 24.0°, 27.4°, 31.2° and 39.5°, +0.2° for each, appeared in powder X-ray diffractometry using Cu Kα radiation.

Apparatus: M18XCE, manufactured by MAC Science, Co. Ltd.
  X-ray: Cu/40 kV tube voltage/100 mA tube current
  Divergence slit: 1°
  Scattering slit: 1°
  Receiving slit: 0.3 mm
  Scan speed: 4.000°/min.
  Sampling width: 0.02°

The obtained solids were crystalline.

Example 2

Production of Crystals of PQQ Disodium Salt

To the mixture of 500 mL of ion-exchanged water and 500 mL of ethanol, 60 g of the solids of PQQ trisodium salt prepared in Reference Example 1, which contain 20 g of PQQ, was added. At this time, the solids were not completely dissolved. To the resulting mixture, hydrochloric acid was added to adjust pH to 3.5. The addition of hydrochloric acid was carried out by slowly adding hydrochloric acid dropwise to the mixture for about 2 hours. After the pH became stable, the mixture was filtered, and crystals of PQQ disodium salt were thereby obtained in a yield of 99 mol %. Although the purity of PQQ contained in the raw material PQQ trisodium salt was 99.0% as measured by liquid chromatography, the purity of PQQ in the obtained PQQ disodium salt was 99.5%, which corresponded to 0.5% increase.

After drying the thus obtained crystals under reduced pressure, powder X-ray diffractometry was carried out in the same manner as in Example 1, and, as a result, the same results as in Example 1 were obtained (Thermal Analysis)

The obtained solids were subjected to thermogravimetry (TG) and differential thermal analysis (DSC) using Thermo plus EVO TG8120 manufactured by Rigaku Corporation. The temperature was increased under air flow at a rate of 10° C./minute.

Figure 2:
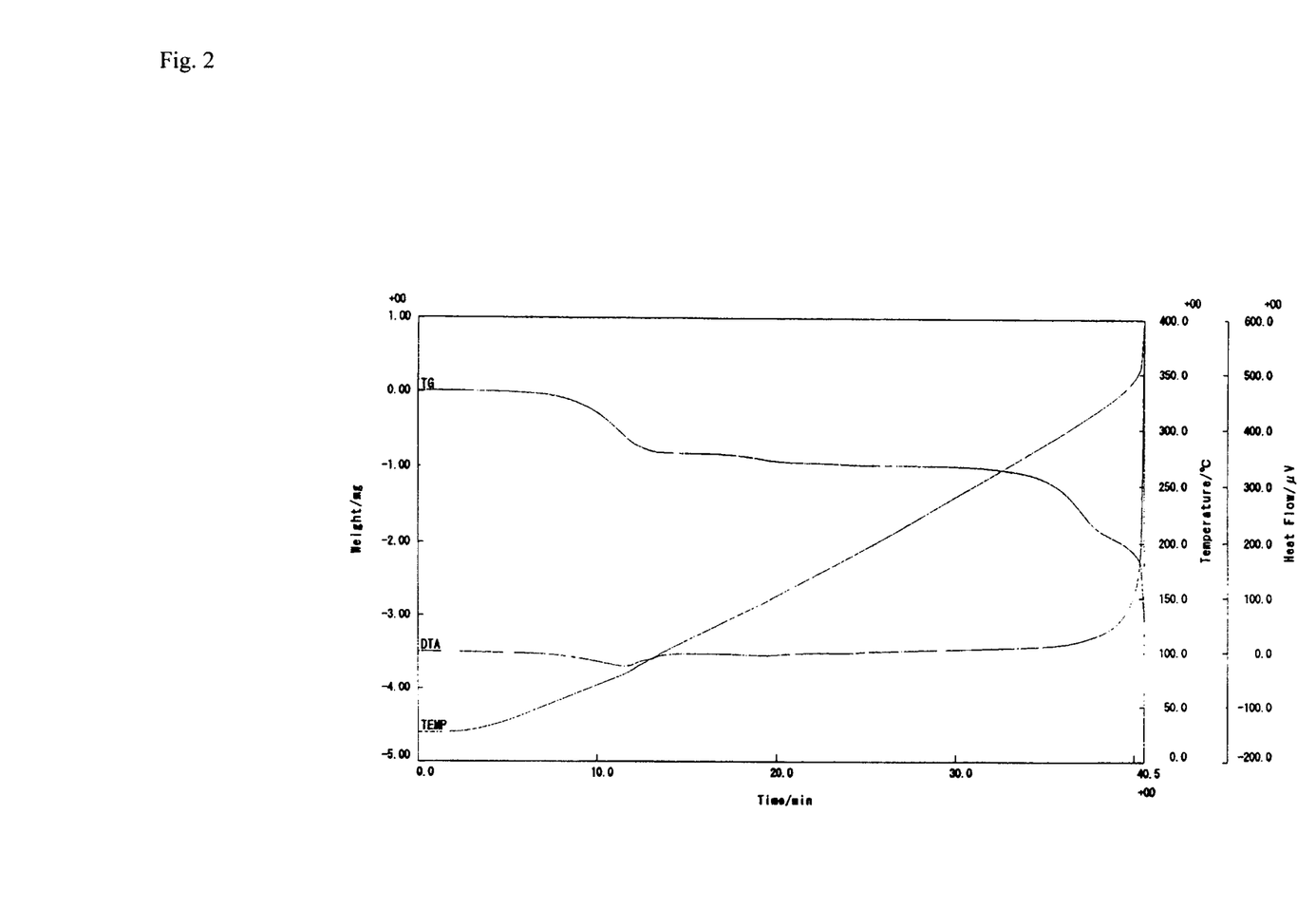
FIG. 2 is a diagram showing data from thermal analysis of the crystals obtained in Example 1.

The results are shown in FIG. 2. Except for occurrence of evaporation of water at about 100° C., there was no change until the temperature increased to 270° C., so that the substance was confirmed to be very stable.

The solids were analyzed by gas chromatography under the conditions described below, and, as a result, no residual ethanol was observed.

(Analysis of Residual Ethanol in Solids)

In 0.5 mL of distilled water, 50 mg of the obtained solids were suspended, and ethanol contained in the supernatant obtained by centrifugation was analyzed under the following conditions to determine the ethanol content in the solids.
  Apparatus: Gas chromatography GC-2014, manufactured by Shimadzu Corporation
  Detection: FID, 210° C.
  Carrier: High-purity nitrogen, 40 mL/min.

Example 3

Crystals of PQQ Trisodium Salt

Figure 3:
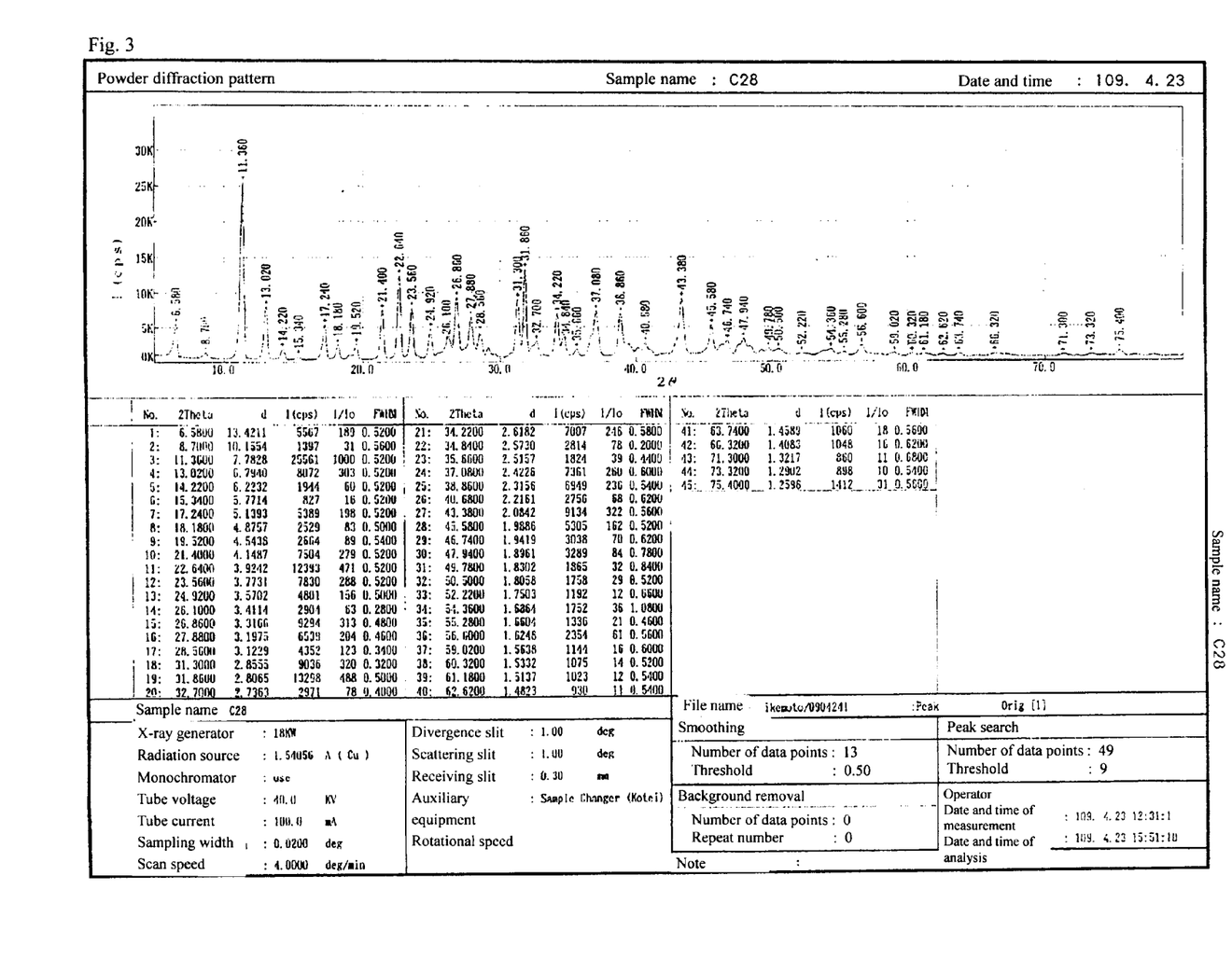
FIG. 3 is a diagram showing a powder X-ray diffraction spectrum of the crystals obtained in Example 3.

The PQQ trisodium salt prepared in Reference Example 1 was completely dissolved in ion-exchanged water, to prepare 500 g of a solution containing 12 g/L PQQ. Based on measurement with a pH meter, pH of the liquid was 7.0. To this liquid, 25 g of dietary salt was added. At this time, red solids were precipitated. After stirring the resulting mixture at room temperature for 1 hour, crystals were recovered by suction filtration and dried under reduced pressure at room temperature for 16 hours. As a result, crystals of PQQ trisodium salt were obtained in a yield of 98 mol %. The powder X-ray diffraction spectrum of the obtained crystals was measured under the conditions described below. The results are shown in FIG. 3. Peaks at 2θ of 6.6°, 11.4°, 13.0°, 22.6°, 26.9°, 27.9°, 37.0°, 38.9° and 43.4°, ±0.2° for each, appeared in powder X-ray diffractometry using Cu Kα radiation.

Apparatus: M18XCE, manufactured by MAC Science, Co. Ltd.
X-ray: Cu/40 kV tube voltage/100 mA tube current
Divergence slit: 1°
Scattering slit: 1°
Receiving slit: 0.3 mm
Scan speed: 4.000°/min.
Sampling width: 0.02°
The obtained solids were crystalline.

Example 4

Crystals of PQQ Trisodium Salt

The PQQ trisodium salt prepared in Reference Example 1 was completely dissolved in ion-exchanged water, to prepare 500 g of a solution containing 12 g/L PQQ. Based on measurement with a pH meter, pH of the liquid was 7.0. To this liquid, 500 mL of ethanol was added. At this time, red solids were precipitated. After stirring the resulting mixture at room temperature for 1 hour, crystals were recovered by suction filtration and dried under reduced pressure at room temperature for 16 hours. As a result, crystals of PQQ trisodium salt were obtained in a yield of 89 mol %. The X-ray diffraction spectrum of the obtained powder of crystals was measured under the same conditions as in Example 3.

As a result, peaks at the same positions as in Example 3 were observed.

In the same manner as in Example 2, thermal analysis and analysis of the residual ethanol in the solids were carried out, and, as a result, the solids were confirmed to have very high thermal stability, and no residual ethanol was observed.

Comparative Example 1

Precipitation of Solids of PQQ Disodium Salt by Ethanol Recrystallization

The PQQ trisodium salt prepared in Reference Example 1 was completely dissolved in ion-exchanged water, to prepare 800 g of a solution containing 10 g/L PQQ. Hydrochloric acid was added to the solution to adjust the pH to 3.5, and 200 mL of ethanol was then added to the solution. At this time, red solids were precipitated. After stirring the resulting mixture at room temperature for 5 hours, the mixture was left to stand at 5° C. for 24 hours, to precipitate solids. The solids were recovered by continuous centrifugation, and dried at 50° C. under reduced pressure.

Figure 4:
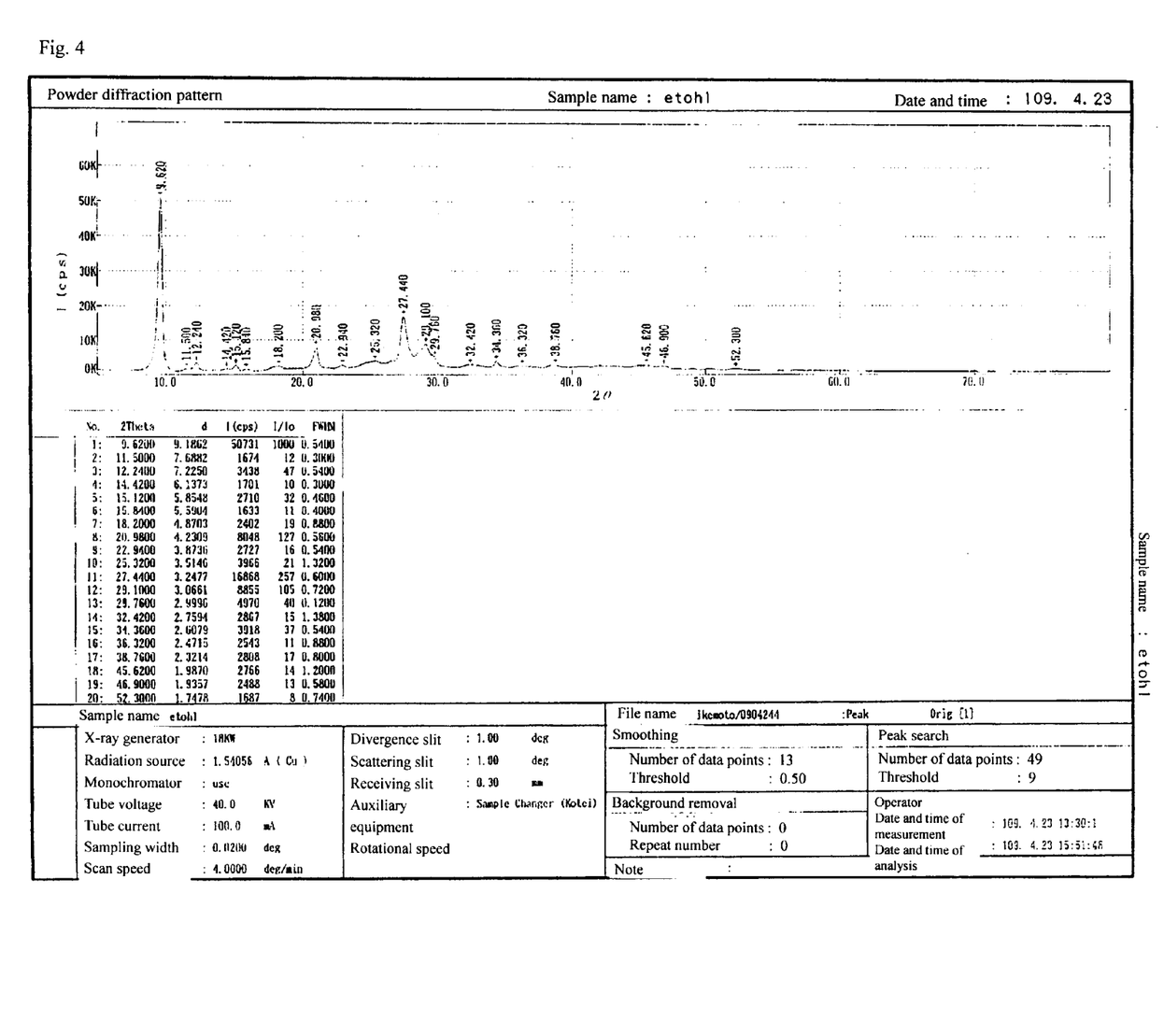
FIG. 4 is a diagram showing a powder X-ray diffraction spectrum of the solids obtained in Comparative Example 1 by the recrystallization method.

The powder X-ray diffraction spectrum of the obtained solids was measured under the same conditions as in Example 1. The results are shown in FIG. 4. Since the obtained solids hardly showed peaks except for those in the low-angle side, these were confirmed to have low crystallinity.

The solids were analyzed by gas chromatography under the same conditions as in Example 2, and, as a result, 0.02% residual ethanol was observed in the solids.

Further, in the same manner as in Example 2, thermal analysis was carried out, and, as a result, reduction in the weight was observed from about 30° C., so that the solids were confirmed to be unstable.

Comparative Example 2

Precipitation of Solids of PQQ Disodium Salt by Crystallization in Methanol

The experiment of crystallization of solids of PQQ disodium salt described in Patent Document 2 was reproduced and the obtained crystals were compared with those of the present invention.

Figure 5:
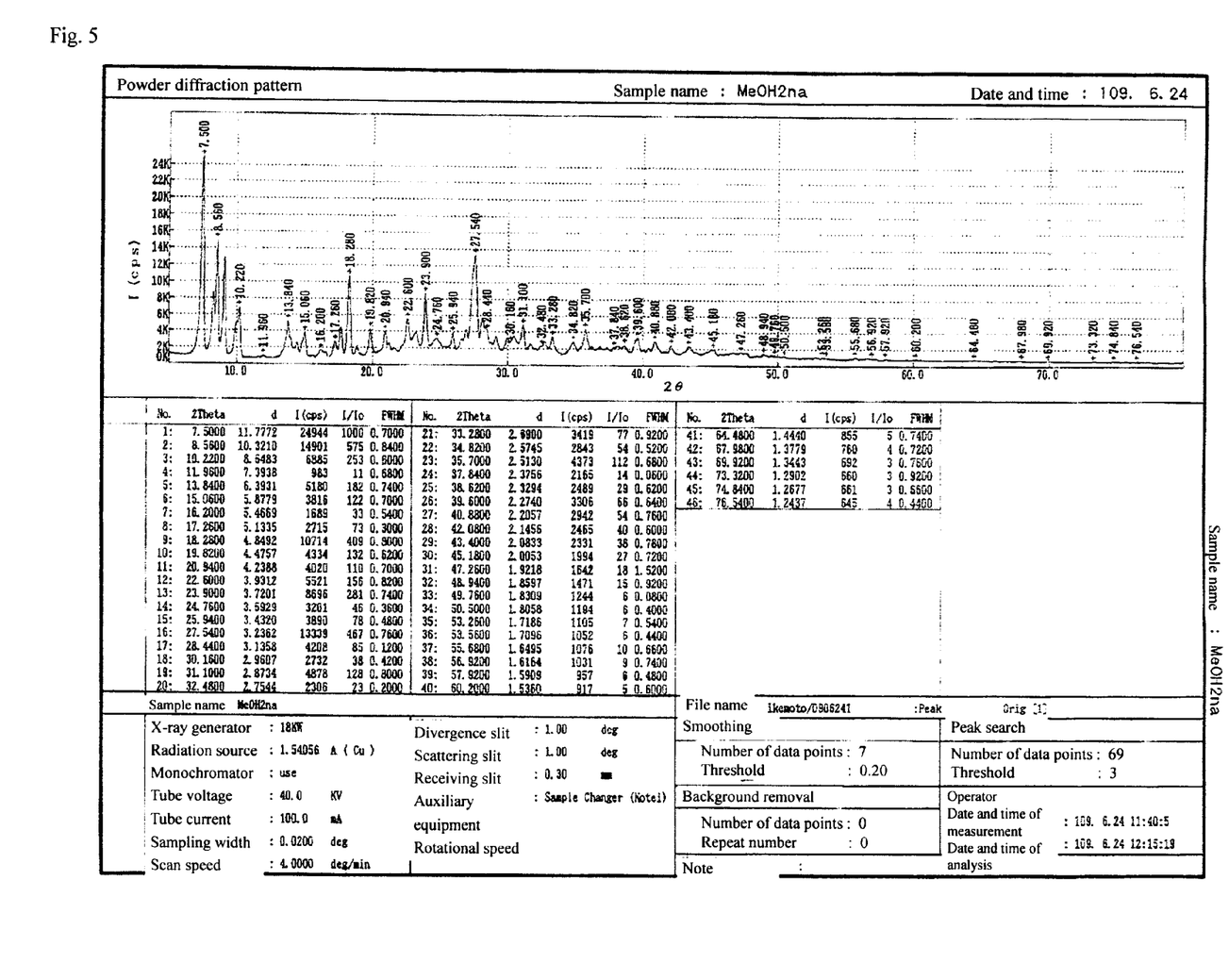
FIG. 5 is a diagram showing a powder X-ray diffraction spectrum of the solids obtained in Comparative Example 2 by crystallization in methanol.

In 30 mL of water at about 60° C., 0.21 g of the crystals of PQQ disodium salt obtained in Example 1 were dissolved. To this solution, 50 g of methanol was added. At the time of the mixture, the solution was uniform. By leaving the solution to stand at 4° C. overnight, solids were precipitated. The mixture was centrifuged and dried under reduced pressure, and the powder X-ray diffraction spectrum of the obtained solids was then measured under the same conditions as in Example 1. The results are shown in FIG. 5. Peaks at positions different from those observed in Examples 1 and 2 in the present application were observed.

Further, in the same manner as in Example 2, thermal analysis and analysis of the residual ethanol in the solids were carried out, and, as a result, the solids were confirmed to have low thermal stability, and residual ethanol was observed.

Comparative Example 3

Conversion of Single Crystal Data to Powder X-Ray Data

For the PQQ disodium salt reported in JACS, vol. 111, pp. 6822-6828 (1989), the data of X-ray crystallography of single crystals described in this literature were used to simulate how peaks appear in powder X-ray diffractometry of these crystals.

Figure 6:
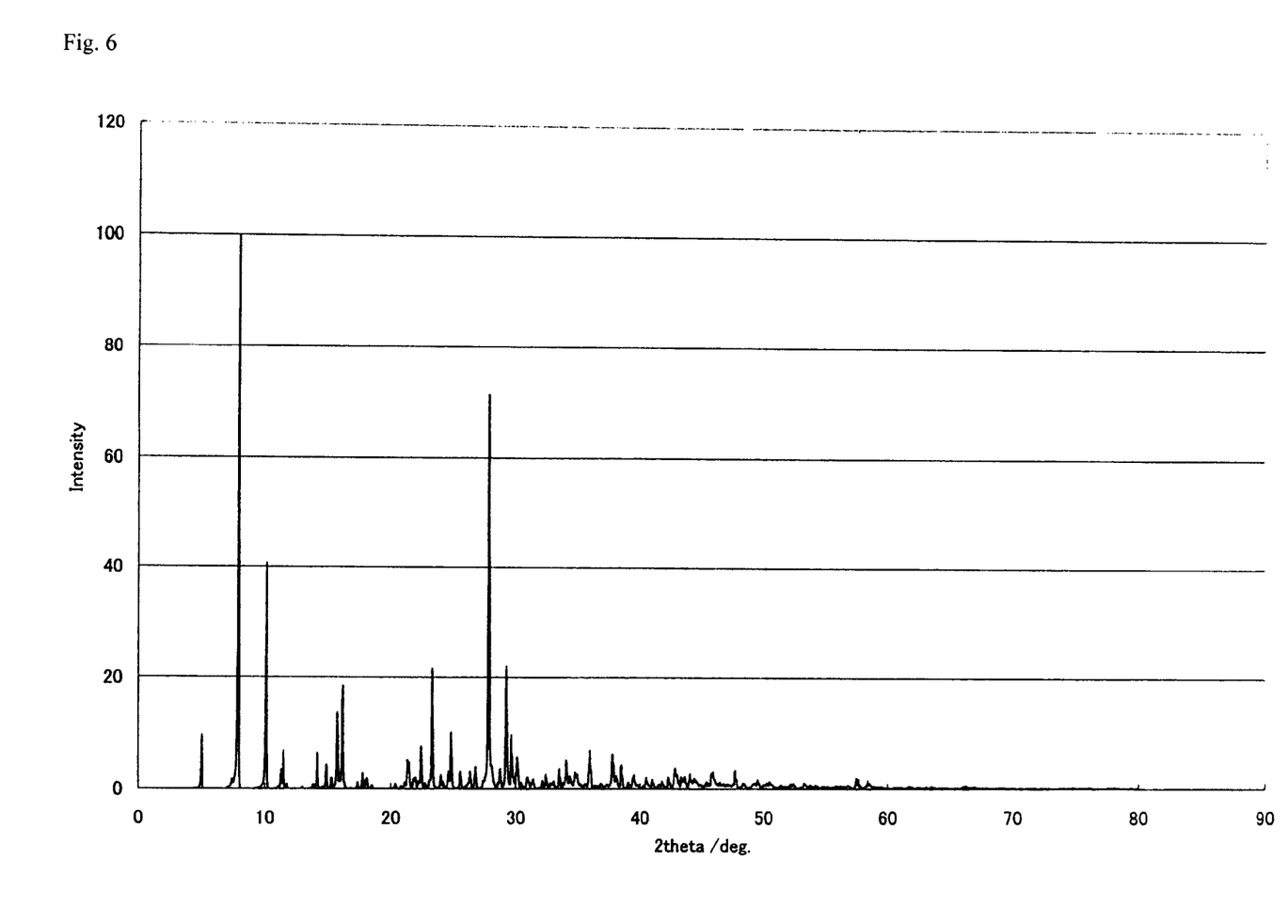
FIG. 6 is a diagram showing a powder X-ray diffraction spectrum obtained by the simulation in Comparative Example 3 using single-crystal data.

Results of calculation using analysis software RIETAN2000 with WINDOWS (registered trademark) XP and a personal computer having a CPU of not less than 1 GHz are shown in FIG. 6.

As shown therein, there are peaks at positions different from those in the cases of the crystals of the present invention.

The results from Examples 1 and 3 and Comparative Examples 1, 2 and 3 are summarized below in Table 1.

TABLE 1

| | Example 1 | Comparative Example 1 | Example 3 | Comparative Example 2 | Comparative Example 3 |
| --- | --- | --- | --- | --- | --- |
| PQQ salt composition | Disodium salt | Disodium salt | Trisodium salt | Disodium salt | Disodium salt |
| Crystallization method | Example 1 | Comparative Example 1 | Example 3 | Comparative Example 2 | Comparative Example 3 |
| 2θ | 9.1 | 9.7 | 6.6 | 7.5 | 5.1 |
| | 10.3 | 21.1 | 11.4 | 8.6 | 7.9 |
| | 13.8 | 27.5 | 13.0 | 10.2 | 10.1 |

TABLE 1-continued

| Example 1 | Comparative Example 1 | Example 3 | Comparative Example 2 | Comparative Example 3 |
|---|---|---|---|---|
| 17.7 | | 22.6 | 13.8 | 15.8 |
| 18.3 | | 26.9 | 18.3 | 16.2 |
| 24.0 | | 27.9 | 22.6 | 23.3 |
| 27.4 | | 37.0 | 23.9 | 27.8 |
| 31.2 | | 38.9 | 27.5 | 29.2 |
| 39.5 | | 43.4 | | |

The values at 2θ were clearly different from each other, suggesting that the crystals have different crystal forms. It was shown that the crystal forms of the present invention are novel.

INDUSTRIAL APPLICABILITY

The PQQ crystals of the present invention are useful in the fields of pharmaceuticals, functional foods and the like.

The invention claimed is:

1. A crystal of pyrroloquinoline quinone disodium salt having peaks at 2θ of 9.1°, 10.3°, 13.8°, 17.7°, 18.3°, 24.0°, 27.4°, 31.2° and 39.5° (±0.2° for each) in powder X-ray diffractometry using Cu Kα radiation.

2. A crystal of pyrroloquinoline quinone trisodium salt having peaks at 2θ of 6.6°, 11.4°, 13.0°, 22.6°, 26.9°, 27.9°, 37.0°, 38.9° and 43.4° (±0.2° for each) in powder X-ray diffractometry using Cu Kα radiation.

3. A method for producing the crystal of pyrroloquinoline quinone disodium salt of claim 1, the method comprising:
   (i) preparing a mixture comprising pyrroloquinoline quinone trisodium salt, a water-soluble organic solvent, and water, wherein the mixture is an aqueous solution, an aqueous suspension, or both, and wherein the mixture comprises 10 to 90 (v/v) % of the water-soluble organic solvent, and
   (ii) adjusting a pH of the mixture to within a range of 2 to 5 to obtain a crystal of pyrroloquinoline quinone disodium salt.

4. The method of claim 3, wherein the water-soluble organic solvent is an alcohol.

5. The method of claim 4, wherein the alcohol is ethanol.

6. The method of claim 3 wherein the mixture is an aqueous suspension.

7. A method for producing the crystal of pyrroloquinoline quinone trisodium salt of claim 2, the method comprising:
   (i) preparing a first mixture comprising water and pyrroloquinoline quinone trisodium salt, wherein the mixture is an aqueous solution, an aqueous suspension, or both,
   (ii) adding a water-soluble organic solvent to the first mixture to obtain a second mixture comprising 10 to 90 (v/v) % of the water-soluble organic solvent, while maintaining a pH of the second mixture within a range of 6 to 10, to obtain a crystal of pyrroloquinoline quinone trisodium salt.

8. The method of claim 7, wherein the water-soluble organic solvent is an alcohol.

9. The method of claim 8, wherein the alcohol is ethanol.

10. A method for producing the crystal of pyrroloquinoline quinone trisodium salt of claim 2, the method comprising:
   (i) preparing a mixture comprising water and pyrroloquinoline quinone trisodium salt, wherein the mixture is an aqueous solution, an aqueous suspension, or both,
   (ii) performing salting-out on the mixture while maintaining a pH within a range of 6 to 10, to obtain a crystal of pyrroloquinoline quinone trisodium salt.

11. A pharmaceutical comprising the crystal of a sodium salt of pyrroloquinoline quinone of claim 1.

12. A pharmaceutical comprising the crystal of a sodium salt of pyrroloquinoline quinone of claim 2.

13. The method of claim 3 wherein the mixture comprises 20 to 80 (v/v) % of the water-soluble organic solvent.

14. The method of claim 7 wherein the mixture comprises 20 to 80 (v/v) % of the water-soluble organic solvent.

15. The crystal of claim 1, having a purity of 99.5% or higher as assayed by high performance liquid chromatography.

16. A method for producing the crystal of pyrroloquinoline quinone disodium salt of claim 1, the method comprising:
   (i) preparing a first mixture comprising water and pyrroloquinoline quinone trisodium salt, wherein the mixture is an aqueous solution, an aqueous suspension, or both,
   (ii) adding a water-soluble organic solvent to the first mixture to obtain a second mixture comprising 10 to 90 (v/v) % of the water-soluble organic solvent, and
   (iii) adjusting a pH of the second mixture to within a range of 2 to 5 to obtain a crystal of pyrroloquinoline quinone disodium salt.

17. A method for producing the crystal of pyrroloquinoline quinone disodium salt of claim 1, the method comprising:
   (i) preparing a first mixture comprising a water-soluble organic solvent and pyrroloquinoline quinone trisodium salt, wherein the mixture is a solution, a suspension, or both,
   (ii) adding water to the first mixture to obtain a second mixture comprising 10 to 90 (v/v) % of the water-soluble organic solvent, and
   (iii) adjusting a pH of the second mixture to within a range of 2 to 5 to obtain a crystal of pyrroloquinoline quinone disodium salt.

18. A method for producing the crystal of pyrroloquinoline quinone trisodium salt of claim 2, the method comprising:
   (i) preparing a first mixture comprising a water-soluble organic solvent and pyrroloquinoline quinone trisodium salt, wherein the mixture is a solution, a suspension, or both,
   (ii) adding water to the first mixture to obtain a second mixture comprising 10 to 90 (v/v) % of the water-soluble organic solvent, while maintaining a pH of the second mixture within a range of 6 to 10, to obtain a crystal of pyrroloquinoline quinone trisodium salt.

* * * * *

UNITED STATES PATENT AND TRADEMARK OFFICE
CERTIFICATE OF CORRECTION

PATENT NO. : 9,163,014 B2
APPLICATION NO. : 13/383472
DATED : October 20, 2015
INVENTOR(S) : Junichi Edahiro et al.

It is certified that error appears in the above-identified patent and that said Letters Patent is hereby corrected as shown below:

On the title page, Item (56), reference Ishida, T., et al., "Molecular and Crystal Structures of PQQ (Methoxatin), a Novel Coenzyme of Quinoproteins : Extensive Stacking Character and Metal Ion Interaction", Journal of American Chemical Society, vol. 111, pp. 6822-6828, (1989)" should read -- "Molecular and Crystal Structure of PQQ (Methoxatin), a Novel Coenzyme of Quinoproteins : Extensive Stacking Character and Metal Ion Interaction", Journal of American Chemical Society, vol. 111, pp. 6822-6828, (1989) --.

Claims

Column 11, line 52, "suspension, or both," should read -- suspension, or both, and --.

Column 12, line 14, "suspension, or both," should read -- suspension, or both, and --.

Column 12, line 56, "both," should read -- both, and --.

Signed and Sealed this
Twenty-first Day of June, 2016

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 9,163,014 B2 |
| APPLICATION NO. | : 13/383472 |
| DATED | : October 20, 2015 |
| INVENTOR(S) | : Junichi Edahiro et al. |

It is certified that error appears in the above-identified patent and that said Letters Patent is hereby corrected as shown below:

On the title page, Item (75), Inventors, "Junichi Edahiro, Niigata (JP); Hitoshi Sakamoto, Niigata (JP); Kazuto Ikemoto, Niigata (JP); Hajime Shimizu, Niigata (JP); Tatsuya Hasegawa, Niigata (JP)" should read -- Junichi Edahiro, Niigata (JP); Hitoshi Sakamoto, Niigata (JP); Kazuto Ikemoto, Niigata (JP); Hajime Shimizu, Niigata (JP); Tatsuya Hasegawa, Niigata (JP); Masahiko Nakano, Niigata (JP) --.

Signed and Sealed this
Nineteenth Day of July, 2016

Michelle K. Lee
*Director of the United States Patent and Trademark Office*